(12) United States Patent
Beazley et al.

(10) Patent No.: US 7,964,348 B2
(45) Date of Patent: Jun. 21, 2011

(54) COTTON EVENT PV-GHBK04 (531) AND COMPOSITIONS AND METHODS FOR DETECTION THEREOF

(75) Inventors: Kim A Beazley, Kirkwood, MO (US); Jeanna R Hillyard, St. Charles, MO (US); Shengzhi Pang, Ellisville, MO (US); James K Roberts, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/801,114

(22) Filed: May 8, 2007

(65) Prior Publication Data

US 2008/0124724 A1 May 29, 2008

Related U.S. Application Data

(62) Division of application No. 10/416,877, filed as application No. PCT/US01/43297 on Nov. 20, 2001, now abandoned.

(60) Provisional application No. 60/252,124, filed on Nov. 20, 2000.

(51) Int. Cl.
C12Q 1/68 (2006.01)
C07H 21/02 (2006.01)

(52) U.S. Cl. ............................ 435/6; 435/975; 536/23.1

(58) Field of Classification Search ........................ None
See application file for complete search history.

(56) References Cited

U.S. PATENT DOCUMENTS

| | | | | |
|---|---|---|---|---|
| 5,474,796 | A * | 12/1995 | Brennan | 427/2.13 |
| 5,689,052 | A | 11/1997 | Brown et al. | |
| 6,582,908 | B2 * | 6/2003 | Fodor et al. | 506/9 |
| 2001/0053519 | A1 * | 12/2001 | Fodor et al. | 435/6 |

FOREIGN PATENT DOCUMENTS

WO    WO 00 26371 A    5/2000

OTHER PUBLICATIONS

New England Biolabs 1998/99 Catalog (NEB Catalog).*
Stratagene ("Gene Characterization Kits" 1988).*
Schuler, M.A., et al., "Soybean 7s seed storage protein alpha subunit gene," *Database EMBL Online* Jun. 13, 1985, Database accession No. J01293.
Windels, P., et al., Development of a line specific GMO detection method—a case study, *Med. Fac. Landbouww. Univ. Gent.* 64(5b):459-462 (1999).
Perlak, F.J., et al., Insect resistant cotton plants, *Bio/Technology* 8(10):939-943 (1990).
Liu, Y-G, et al., Efficient isolation and mapping of *Arabidopsis thaliana* T-DNA insert junctions by thermal asymmetric interlaced PCT, *Plant Journal* 8(3):457-463 (1995).
Greenplate, John T., Quantification of *Bacillus thuringiensis* insect control protein Cry1Ac over time in bollgard cotton fruit and terminals, *Journal of Economic Entomology* 92(6):1377-1383 (1999).
Cutler, Sean R., et al., Random GFP::cDNA fusions enable visualization of subcellular structures in cells of *Arabidopsis* at a high frequency, *Proceedings of the National Academy of Sciences USA* 97(7):3718 3723 (2000).
GenBank accession No. AF218816 [Cutler, et al.], Date: Apr. 6, 2000.
Xiang, Chengbin, et al., A mini binary vector series for plant transformation, *Plant Molecular Biology* 40:711 717 (1999).
GenBank accession No. AF139061 [Xiang, et al.], Date: Sep. 23, 1999.

* cited by examiner

*Primary Examiner* — Christopher M. Babic
(74) *Attorney, Agent, or Firm* — Timothy K. Ball; Winston & Strawn LLP

(57) ABSTRACT

The present invention provides assays for detecting the presence of the 531 cotton event nucleic acid sequences in a biological sample based on the DNA sequence of the recombinant construct inserted into the cotton genome and of genomic sequences flanking the insertion site in a cotton genome.

11 Claims, 3 Drawing Sheets

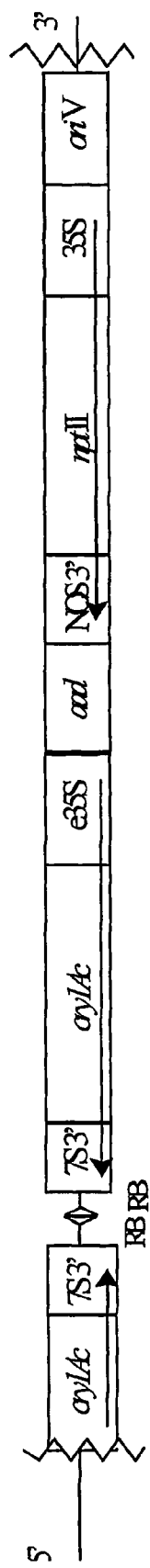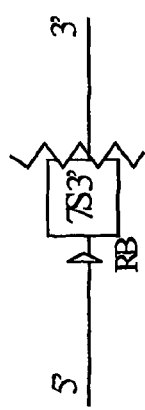
FIG. 1A
FIG. 1B

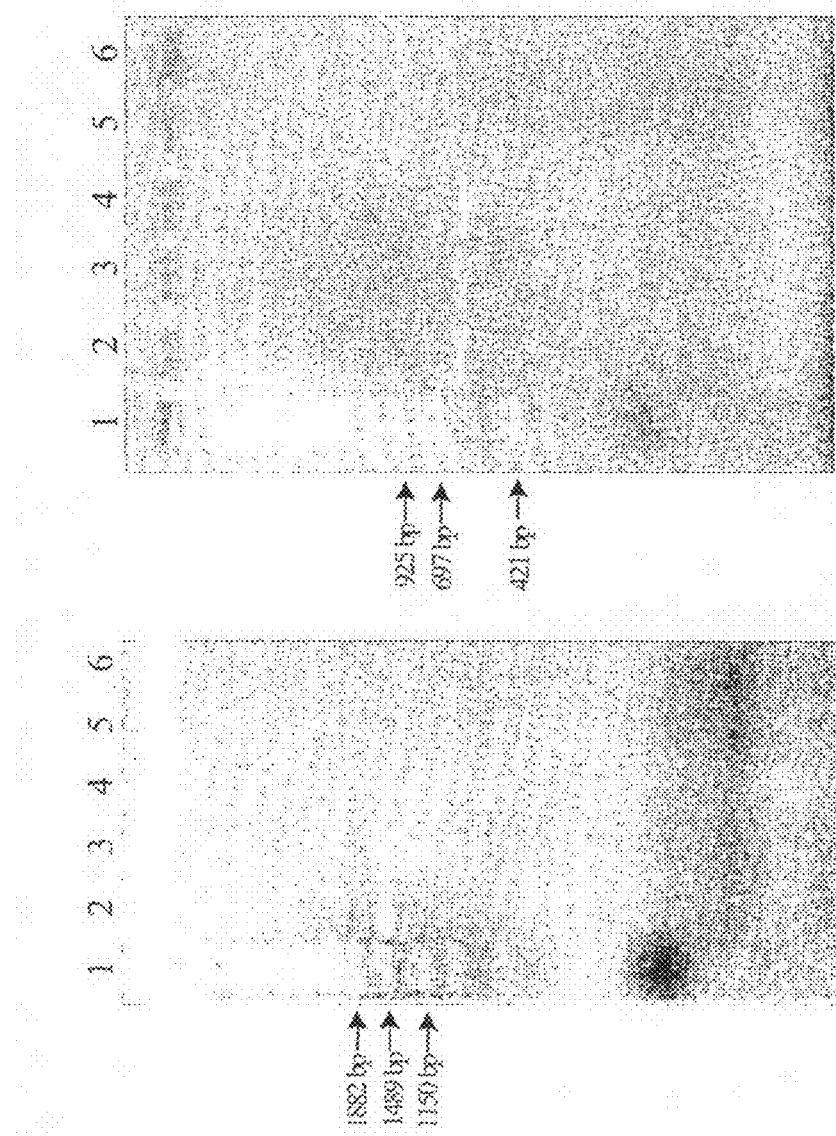
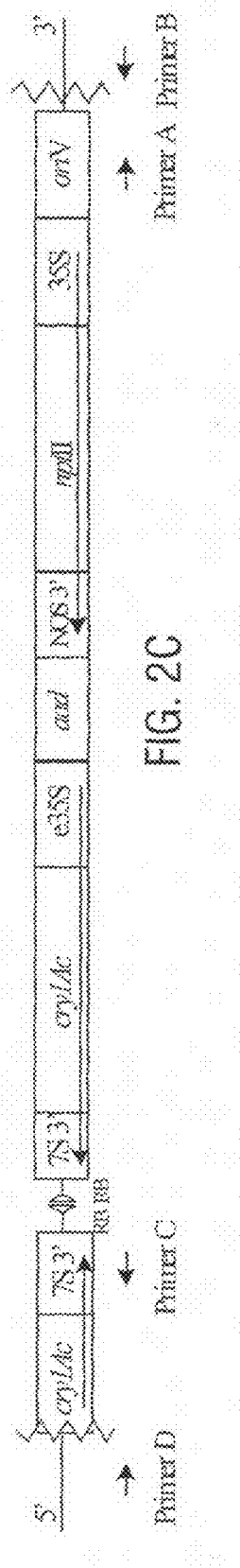
FIG. 2A
FIG. 2B
FIG. 2C

SEQUENCE LISTING

<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Synthetic
<220> FEATURE:

-continued

```
<221> NAME/KEY: misc_feature
<222> LOCATION: (1)..(20)
<223> OTHER INFORMATION: 3' primary, functional insert - (Gossypium
      hirsutum) genome junction

<400> SEQUENCE: 1
gcgtttctgg ttataatata                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: 3' partial cry1Ac insert-cotton (Gossypium
      hirsutum) genome junction

<400> SEQUENCE: 2
tgacccactt agcagagaag                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: 5' partial termination sequence insert-cotton
      (Gossypium hirsutum) genome junction

<400> SEQUENCE: 3
gagtgtgtaa caaacactga                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: 3' partial termination sequence insert -
      cotton (Gossypium hirsutum) genome junction

<400> SEQUENCE: 4
aatacactca cctgccgaat                                              20

<210> SEQ ID NO 5
<211> LENGTH: 1104
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1104)
<223> OTHER INFORMATION: 3' partial cry1aC insert sequence

<400> SEQUENCE: 5
agcagagaag aagtggaggg acaaacgtga gaaactcgaa tgggaaacta acatcgttta    60
caaggaggcc aaagagtccg tggatgcttt gttcgtgaac tcccaatatg atcagttgca   120
agccgacacc aacatcgcca tgatccacgc cgcagacaaa cgtgtgcaca gcattcgtga   180
```

```
ggcttacttg cctgagttgt ccgtgatccc tggtgtgaac gctgccatct tcgaggaact    240
tgagggacgt atctttaccg cattctcctt gtacgatgcc agaaacgtca tcaagaacgg    300
tgacttcaac aatggcctca gctgctggaa tgtgaaaggt catgtggacg tggaggaaca    360
gaacaatcag cgttccgtcc tggttgtgcc tgagtgggaa gctgaagtgt cccaagaggt    420
tagagtctgt ccaggtagag gctacattct ccgtgtgacc gcttacaagg agggatacgg    480
tgagggttgc gtgaccatcc acgagatcga gaacaacacc gacgagctta agttctccaa    540
ctgcgtcgag gaagaaatct atcccaacaa caccgttact tgcaacgact acactgtgaa    600
tcaggaagag tacggaggtg cctacactag ccgtaacgga ggttacaacg aagctccttc    660
cgttcctgct gactatgcct ccgtgtacga ggagaaatcc tacacagatg cagacgtga    720 gaacccttgc gagttcaaca gaggttacag ggactacaca ccacttccag ttggctatgt    780
taccaaggag cttgagtact ttcctgagac cgacaaagtg tggatcgaga tcggtgaaac    840
cgagggaacc ttcatcgtgg acagcgtgga gcttctcttg atggaggaat aatgagatct    900
agaggcctga attcgagctc ggtacccggg gatcccgtcc tttgtcttca attttgaggg    960 cttttttactg aataagtatg tagtactaaa atgtatgctg taatagctca tagtgagcga   1020
ggaaagtatc gggctatttta actatgactt gagctccatc tatgaataaa taaatcagca   1080
tatgatgctt ttgttttgtg tact                                         1104

<210> SEQ ID NO 6
<211> LENGTH: 309
<212> TYPE: DNA
<213> ORGANISM: Gossypium hirsutum
<220> FEATURE:
<221> NAME/KEY: Unsure
<222> LOCATION: (1)..(309)
<223> OTHER INFORMATION: A cotton (Gossypium hirsutum) genome sequence
      flanking 5' partial cry1Ac insert

<400> SEQUENCE: 6
aagcaagttt caaacccaga attgaacatt gaattccttc ccactcgatc aaccaataac     60
atacttggtt tatatatata taaatgagtc ccctattcta tttcctccat tcccccccc    120 ctccccggta cggatgagta ggcctactct tttttttcata gttgtttttt agccgattta    180
agagatgaaa attcagacaa tgcaataggg aaggtcattg atgtacacca aagagaaacc    240
ccaatcataa aagtatatgc gacaaaacgc gttgaaatta aaaaccaatg ccaccccact    300
gacccactt                                                          309

<210> SEQ ID NO 7
<211> LENGTH: 391
<212> TYPE: DNA
<213> ORGANISM: Gossypium hirsutum
<220> FEATURE:
<221> NAME/KEY: Unsure
<222> LOCATION: (1)..(391)
<223> OTHER INFORMATION: A cotton (Gossypium hirsutum) genome sequence
      flanking 5' end of full length primary, functional insert
      sequence.

<400> SEQUENCE: 7
aaatcgttcg tctgacttgg gtatagggcc gaaagactaa tcgaaccgtc tagtagctgg     60
ttccctccga agtttccctc aggatagctg agcccttag cgagttctat cgggtaaagc    120
caatgattag aggcatcggg ggcgcaacgc cctcgaccta ttctcaaact ttaaataggt    180 aggacgcgc ggctgcttcg ttgagccgcg ccacggaatc gagagctcca agtgggccat    240
ttttggtaag cagaactggc gatgcgggat gaaccggaag ccgggttacg gtgcccaact    300
```

```
gcgcgctaac ctagaaccca caaagggtgt tggtcgatta agacagcagg acggtggtca    360
tggaagtcga aatccgctaa ggagtgtgta a                                   391

<210> SEQ ID NO 8
<211> LENGTH: 242
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(242)
<223> OTHER INFORMATION: 5' partial termination insert sequence

<400> SEQUENCE: 8
caaacactga tagtttaaac tgaaggcggg aaacgacaat ctgatcccag cttgcatgcc    60
tgcaggtcaa ttcaatattg tggcaggaca ttgctacatg atacctctta gaattgttta   120
gacttcagat cgatcttgtc agtctgaaag acccaaaaac aaatgcaatt tcttttctgg   180
tagaccgtga caatttgtct aagatgtatc tgatttaatg cctttgtat ataatacact    240 ca                                                                   242

<210> SEQ ID NO 9
<211> LENGTH: 356
<212> TYPE: DNA
<213> ORGANISM: Gossypium hirsutum
<220> FEATURE:
<221> NAME/KEY: Unsure
<222> LOCATION: (1)..(356)
<223> OTHER INFORMATION: cotton (Gossypium hirsutum) genome flanking
      3' partial terminaton sequence of the insert

<400> SEQUENCE: 9
cctgccgaat caactagccc cgaaaatgga tggcgcttaa gcgcgcgacc tatacccggc    60
cgtcggggca agggccaggc cccgatgagt aggagggcgc ggcggtcgcc gcaaaacccg   120
gggcgcgagc ccgggcggag cggccgtcgg tgcagatctt ggtggtagta gcaaatattc   180
aaatgagaac tttgaaggcc gaagagggga aaggttccat gtgaacggca cttgcacatg   240
ggttagtcga tcctaagaga cgggggaagc ccgtccgaca gcgcgtccag cgcgagcttc   300
gaaagggaat cgggttaaaa ttcctgaacc gggacgcggc ggctgacggc aacgtt       356

<210> SEQ ID NO 10
<211> LENGTH: 378
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(378)
<223> OTHER INFORMATION: 3' primary functional insert, insert sequence

<400> SEQUENCE: 10
cccctcaaat gtcaataggt gcgcccctca tctgtcagca ctctgcccct caagtgtcaa    60
ggatcgcgcc cctcatctgt cagtagtcgc gcccctcaag tgtcaatacc gcagggcact   120
tatccccagg cttgtccaca tcatctgtgg gaaactcgcg taaatcagg cgttttcgcc    180 gatttgcgag gctggccagc tccacgtcgc cggccgaaat cgagcctgcc cctcatctgt   240
caacgccgcg ccgggtgagt cggccccctca agtgtcaacg tccgcccctc atctgtcagt   300
gagggccaag ttttccgcga ggtatccaca acgccggcgg ccgcggtgtc tcgcacacgg   360
```
cttcgacggc gtttctgg                                              378

<210> SEQ ID NO 11
<211> LENGTH: 211
<212> TYPE: DNA
<213> ORGANISM: Gossypium hirsutum
<220> FEATURE:
<221> NAME/KEY: Unsure
<222> LOCATION: (1)..(211)
<223> OTHER INFORMATION: A cotton (Gossypium hirsutum) genome sequence
      flanking 3' primary functional insert

<400> SEQUENCE: 11
ttataatata cacatatata atttatcact gtatattctt gcagagaaca atcacgaggc      60
attggcccct ccattttttt aaaaaaaatt tgatctgata gagaaagaa agaaagaaaa     120 agaagaatat tagtgacctt tcaatggtga aaaatcaaaa aaaaatctca tttaatgata    180
aacaaaatgt caaacagtct gacagctcct g                                    211

<210> SEQ ID NO 12
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 12
gccaatgcct cgtgattgtt ctctgc                                          26

<210> SEQ ID NO 13
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 13
gatttgcgag gctggccagc tccacg                                          26

<210> SEQ ID NO 14
<211> LENGTH: 589
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(589)
<223> OTHER INFORMATION: 3' flanking cotton (Gossypium hirsutum)
      genome + primary, functional cry1Ac insert sequence

<400> SEQUENCE: 14
cccctcaaat gtcaataggt gcgcccctca tctgtcagca ctctgcccct caagtgtcaa      60
ggatcgcgcc cctcatctgt cagtagtcgc gcccctcaag tgtcaatacc gcagggcact    120
tatccccagg cttgtccaca tcatctgtgg gaaactcgcg taaaatcagg cgttttcgcc    180
gatttgcgag gctggccagc tccacgtcgc cggccgaaat cgagcctgcc cctcatctgt    240
caacgccgcg ccgggtgagt cggcccctca agtgtcaacg tccgcccctc atctgtcagt    300
gagggccaag ttttccgcga ggtatccaca acgccggcgg ccgcggtgtc tcgcacacgg    360
cttcgacggc gtttctggtt ataatataca catatataat ttatcactgt atattcttgc    420
agagaacaat cacgaggcat tggcccctcc atttttttaa aaaaaatttg atctgataga    480 gaaagaaag aaagaaaaag aagaatatta gtgaccttc aatggtgaaa aatcaaaaaa     540

```
aaatctcatt taatgataaa caaaatgtca aacagtctga cagctcctg        589
```

<210> SEQ ID NO 15
<211> LENGTH: 1413
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1413)
<223> OTHER INFORMATION: 3' flanking cotton (Gossypium hirsutum)
    genome + partial cry1Ac insert sequence

<400> SEQUENCE: 15

```
aagcaagttt caaacccaga attgaacatt gaattccttc ccactcgatc aaccaataac     60
atacttggtt tatatatata taaatgagtc ccctattcta tttcctccat tcccccccc    120
ctccccggta cggatgagta ggcctactct tttttcata gttgttttt agccgattta    180
agagatgaaa attcagacaa tgcaataggg aaggtcattg atgtacacca aagagaaacc    240
ccaatcataa aagtatatgc gacaaaacgc gttgaaatta aaaaccaatg ccaccccact    300
gacccactta gcagagaaga agtggaggga caaacgtgag aaactcgaat gggaaactaa    360
catcgtttac aaggaggcca aagagtccgt ggatgctttg ttcgtgaact cccaatatga    420
tcagttgcaa gccgacacca acatcgccat gatccacgcc gcagacaaac gtgtgcacag    480
cattcgtgag gcttacttgc ctgagttgtc cgtgatccct ggtgtgaacg ctgccatctt    540
cgaggaactt gagggacgta tctttaccgc attctccttg tacgatgcca gaaacgtcat    600
caagaacggt gacttcaaca atggcctcag ctgctggaat gtgaaaggtc atgtggacgt    660
ggaggaacag aacaatcagc gttccgtcct ggttgtgcct gagtgggaag ctgaagtgtc    720
ccaagaggtt agagtctgtc caggtagagg ctacattctc cgtgtgaccg cttacaagga    780
gggatacggt gagggttgcg tgaccatcca cgagatcgag aacaacaccg acgagcttaa    840
gttctccaac tgcgtcgagg aagaaatcta tcccaacaac accgttactt gcaacgacta    900
cactgtgaat caggaagagt acggaggtgc ctacactagc cgtaacagag gttacaacga    960
agctccttcc gttcctgctg actatgcctc cgtgtacgag gagaaatcct acacagatgg   1020
cagacgtgag aaccccttgcg agttcaacag aggttacagg gactacacac cacttccagt   1080
tggctatgtt accaaggagc ttgagtactt tcctgagacc gacaaagtgt ggatcgagat   1140
cggtgaaacc gagggaacct tcatcgtgga cagcgtggag cttctcttga tggaggaata   1200
atgagatcta gaggcctgaa ttcgagctcg gtacccgggg atcccgtcct ttgtcttcaa   1260
ttttgagggc tttttactga ataagtatgt agtactaaaa tgtatgctgt aatagctcat   1320
agtgagcgag gaaagtatcg ggctatttaa ctatgacttg agctccatct atgaataaat   1380
aaatcagcat atgatgcttt tgttttgtgt act                                1413
```

<210> SEQ ID NO 16
<211> LENGTH: 989
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(989)
<223> OTHER INFORMATION: 5' flanking cotton (Gossypium hirsutum)
    genome + partial term. seq. + 3' flanking cotton genome

<400> SEQUENCE: 16

-continued

```
aaatcgttcg tctgacttgg gtataggggc gaaagactaa tcgaaccgtc tagtagctgg      60
ttccctccga agtttccctc aggatagctg gagcccttag cgagttctat cgggtaaagc     120
caatgattag aggcatcggg ggcgcaacgc cctcgaccta ttctcaaact ttaaataggt     180
aggacggcgc ggctgcttcg ttgagccgcg ccacggaatc gagagctcca agtgggccat     240
ttttggtaag cagaactggc gatgcgggat gaaccggaag ccgggttacg gtgcccaact     300
gcgcgctaac ctagaaccca caaagggtgt tggtcgatta agacagcagg acggtggtca     360
tggaagtcga aatccgctaa ggagtgtgta acaaacactg atagtttaaa ctgaaggcgg     420
gaaacgacaa tctgatccca gcttgcatgc ctgcaggtca attcaatatt gtggcaggac     480
attgctacat gataccctctt agaattgttt agacttcaga tcgatcttgt cagtctgaaa    540
gacccaaaaa caaatgcaat ttcttttctg gtagaccgtg acaatttgtc taagatgtat     600
ctgatttaat gccttttgta tataatacac tcacctgccg aatcaactag ccccgaaaat     660
ggatggcgct taagcgcgcg acctatacc  ggcgtcggg gcaagggcca ggccccgatg     720
agtaggaggg cgcggcggtc gccgcaaaac ccggggcgcg agcccgggcg gagcggccgt     780
cggtgcagat cttggtggta gtagcaaata ttcaaatgag aactttgaag gccgaagagg     840
ggaaaggttc catgtgaacg gcacttgcac atgggttagt cgatcctaag agacggggga     900
agcccgtccg acagcgcgtc cagcgcgagc ttcgaaaggg aatcgggtta aaattcctga     960
accgggacgc ggcggctgac ggcaacgtt                                      989
```

<210> SEQ ID NO 17
<211> LENGTH: 27
<212> TYPE: DNA
<213> ORGANISM: Artificial Sequence
<220> FEATURE:
<223> OTHER INFORMATION: Synthetic Oligonucleotide - Primer A

<400> SEQUENCE: 17
tggacagccc ctcaaatgtc aataggt                                         27

<210> SEQ ID NO 18
<211> LENGTH: 27
<212> TYPE: DNA
<213> ORGANISM: Artificial Sequence
<220> FEATURE:
<223> OTHER INFORMATION: Synthetic Oligonucleotide - Primer B

<400> SEQUENCE: 18
aaatattgaa actcatgcag gagctgt                                         27

<210> SEQ ID NO 19
<211> LENGTH: 28
<212> TYPE: DNA
<213> ORGANISM: Artificial Sequence
<220> FEATURE:
<223> OTHER INFORMATION: Synthetic Oligonucleotide - Primer C

<400> SEQUENCE: 19
ttcagcatat ttatacgtgc caagtgcc                                        28

<210> SEQ ID NO 20
<211> LENGTH: 24
<212> TYPE: DNA
<213> ORGANISM: Artificial Sequence
<220> FEATURE:
<223> OTHER INFORMATION: Synthetic Oligonucleotide - Primer D

<400> SEQUENCE: 20
tccgagactc ctagtacctc aact                                          24

<210> SEQ ID NO 21
<211> LENGTH: 28
<212> TYPE: DNA
<213> ORGANISM: Artificial Sequence
<220> FEATURE:
<223> OTHER INFORMATION: Synthetic Oligonucleotide - Primer E

<400> SEQUENCE: 21
ggcattaaat cagatacatc ttagacaa                                      28

<210> SEQ ID NO 22
<211> LENGTH: 23
<212> TYPE: DNA
<213> ORGANISM: Artificial Sequence
<220> FEATURE:
<223> OTHER INFORMATION: Synthetic Oligonucleotide - Primer F

<400> SEQUENCE: 22
ggttcgagtg agagcatgcc tgt                                           23

<210> SEQ ID NO 23
<211> LENGTH: 27
<212> TYPE: DNA
<213> ORGANISM: Artificial Sequence
<220> FEATURE:
<223> OTHER INFORMATION: Synthetic Oligonucleotide - Primer G

<400> SEQUENCE: 23
aaacactgat agtttaaact gaaggcg                                       27

<210> SEQ ID NO 24
<211> LENGTH: 22
<212> TYPE: DNA
<213> ORGANISM: Artificial Sequence
<220> FEATURE:
<223> OTHER INFORMATION: Synthetic Oligonucleotide - Primer H

<400> SEQUENCE: 24
gcttcagatg tctccggact cc                                            22

<210> SEQ ID NO 25
<211> LENGTH: 27
<212> TYPE: DNA
<213> ORGANISM: Artificial Sequence
<220> FEATURE:
<223> OTHER INFORMATION: Synthetic Oligonucleotide - Primer I

<400> SEQUENCE: 25
tagccgattt aagagatgaa aattcag                                       27

<210> SEQ ID NO 26
<211> LENGTH: 28
<212> TYPE: DNA
<213> ORGANISM: Artificial Sequence
<220> FEATURE:
<223> OTHER INFORMATION: Synthetic Oligonucleotide - Primer J

<400> SEQUENCE: 26
caccattgaa aggtcactaa tattcttc                                      28

<210> SEQ ID NO 27
<211> LENGTH: 24
<212> TYPE: DNA
<213> ORGANISM: Artificial Sequence
<220> FEATURE:

```
<223> OTHER INFORMATION: Synthetic Oligonucleotide - Primer L

<400> SEQUENCE: 27
tttggtaagc agaactggcg atgc                                              24

<210> SEQ ID NO 28
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 28
taggtcgcgc gcttaagcgc catc                                              24

<210> SEQ ID NO 29
<211> LENGTH: 209
<212> TYPE: DNA
<213> ORGANISM: Gossypium hirsutum
<220> FEATURE:
<221> NAME/KEY: Unsure
<222> LOCATION: (1)..(209)
<223> OTHER INFORMATION: an amplicon sequence produced using
      SEQ ID NOS: 27 and 28

<400> SEQUENCE: 29
tttggtaaga cgaactggcg atgcgggatg aaccggaagc cgggttacgg tgcccaactg       60
cgcgctaacc tagaacccac aaagggtgtt ggtcgattaa dacagcagga cggtggtcat      120
ggaagtcgaa atccgctaag gagtgtgtaa caactcacct gccgaatcaa ctagccccga      180
aaatggatgg cgcttaagcg cgcgaccta                                        209

<210> SEQ ID NO 30
<211> LENGTH: 374
<212> TYPE: DNA
<213> ORGANISM: Artificial Sequence
<220> FEATURE:
<223> OTHER INFORMATION: Synthetic
<220> FEATURE:
<221> NAME/KEY: Unsure
<222> LOCATION: (1)..(374)
<223> OTHER INFORMATION: An amplicon produced using SEQ ID NOS: 25
      and 26

<400> SEQUENCE: 30
tagccgattt aagagatgaa aattcagaca atgcaatagg gaaggtcatt gatgtacacc       60
aaagagaaac cccaatcata aaagtatatg cgacaaaacg cgttgaaatt aaaaaccaat     120
gccaccccac tgacccactt agctcttctt ttttaccaac aataaattta tatgtgttgg     180
taaaaggtca cacgacacga caacatcatc aattatacat tttggttata atatacacat     240
atataattta tcactgtata ttcttgcaga gaacaatcac gaggcattgg cccctccatt     300
tttttaaaaa aaatttgatc tgatagagaa aagaaagaaa gaaaagaag aatattagtg      360 acctttcaat ggtg                                                        374

<210> SEQ ID NO 31
<211> LENGTH: 491
<212> TYPE: DNA
<213> ORGANISM: Gossypium hirsutum
<220> FEATURE:
<221> NAME/KEY: Unsure
<222> LOCATION: (1)..(491)
<223> OTHER INFORMATION: Part of cotton (Gossypium hirsutum) genome
      nucleotide sequence flanking 5' end of the partial 7S 3' DNA
      sequence
```

```
<400> SEQUENCE: 31
ggttcgagtg agagcatgcc tgtcgggacc cgaaagatgg tgaactatgc ctgagcgggg      60
cgaagccaga ggaaactctg gtggaggccc gcagcgatac tgacgtgcaa atcgttcgtc     120
tgacttgggt atagggggcga aagactaatc gaaccgtcta gtagctggtt ccctccgaag    180
tttccctcag gatagctgga gcccttagcg agttctatcg ggtaaagcca atgattagag     240
gcatcggggg cgcaacgccc tcgacctatt ctcaaacttt aaataggtag gacggcgcgg     300
ctgcttcgtt gagccgcgcc acggaatcga gagctccaag tgggccattt ttggtaagca     360
gaactggcga tgcgggatga accggaagcc gggttacggt gcccaactgc gcgctaacct     420
agaacccaca aagggtgttg gtcgattaag acagcaggac ggtggtcatg gaagtcgaaa     480
tccgctaagg a                                                          491

<210> SEQ ID NO 32
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: cotton genome sequence + 5' end of partial
      7S' sequence

<400> SEQUENCE: 32
gagtgtgtaa caaacactga                                                  20

<210> SEQ ID NO 33
<211> LENGTH: 1121
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1121)
<223> OTHER INFORMATION: cotton (Gossypium hirsutum) genome
      sequence + cry1Ac insert

<400> SEQUENCE: 33
ggttcgagtg agagcatgcc tgtcgggacc cgaaagatgg tgaactatgc ctgagcgggg      60
cgaagccaga ggaaactctg gtggaggccc gcagcgatac tgacgtgcaa atcgttcgtc     120
tgacttgggt atagggggcga aagactaatc gaaccgtcta gtagctggtt ccctccgaag    180
tttccctcag gatagctgga gcccttagcg agttctatcg ggtaaagcca atgattagag     240
gcatcggggg cgcaacgccc tcgacctatt ctcaaacttt aaataggtag gacggcgcgg     300
ctgcttcgtt gagccgcgcc acggaatcga gagctccaag tgggccattt ttggtaagca     360
gaactggcga tgcgggatga accggaagcc gggttacggt gcccaactgc gcgctaacct     420
agaacccaca aagggtgttg gtcgattaag acagcaggac ggtggtcatg gaagtcgaaa     480
tccgctaagg agtgtgtaac aaacactgat agtttaaact gaaggcggga aacgacaatc     540
tgatcccagc ttgcatgcct gcaggtcaat tcaatattgt ggcaggacat tgctacatga     600
tacctcttag aattgtttag acttcagatc gatcttgtca gtctgaaaga cccaaaaaca     660
aatgcaattt cttttctggt agaccgtgac aatttgtcta agatgtatct gatttaatgc     720
cttttgtata taatacactc acctgccgaa tcaactagcc ccgaaaatgg atggcgctta     780
agcgcgcgac ctatacccgg ccgtcggggc aagggccagg ccccgatgag taggagggcg     840
```

-continued

```
cggcggtcgc cgcaaaaccc ggggcgcgag cccgggcgga gcggccgtcg gtgcagatct    900
tggtggtagt agcaaatatt caaatgagaa ctttgaaggc cgaagagggg aaaggttcca    960
tgtgaacggc acttgcacat gggttagtcg atcctaagag acgggggaag cccgtccgac   1020
agcgcgtcca gcgcgagctt cgaaaggaa tcggttaaa attcctgaac cgggacgcgg    1080
cggctgacgg caacgttagg gagtccggag acatctgaag c                      1121
```

US 7,964,348 B2

COTTON EVENT PV-GHBK04 (531) AND COMPOSITIONS AND METHODS FOR DETECTION THEREOF

CROSS REFERENCE TO RELATED APPLICATIONS

This application is a divisional of application Ser. No. 10/416,877 filed May 15, 2003 now abandoned, which is a 371application of PCT/US01/43297 filed Nov. 20, 2001, which claims benefit of priority from U.S. Provisional Patent Application No. 60/252,124, filed Nov. 20, 2000.

FIELD OF THE INVENTION

The present invention relates to the field of plant molecular biology, more specifically the invention relates to cotton event 531, and to assays for detecting the presence of cotton event 531 in a sample.

BACKGROUND OF THE INVENTION

This invention relates to the lepidopteran resistant cotton (*Gossypium hirsutum*) plant 531 and to the detection of the transgene/genomic insertion regions in cotton plant 531 and progeny thereof. The present invention relates to the field of plant molecular biology, more specifically the invention relates to identification of nucleic acids from the transgenic cotton event 531, preferably to assays for detecting the presence of cotton event 531 in a sample and compositions thereof.

Cotton is an important fiber crop in many areas of the world. The methods of biotechnology have been applied to cotton for improvement of the agronomic traits and the quality of the product. The method of introducing transgenes into cotton plants is demonstrated in U.S. Pat. No. 5,004,863. One such agronomic trait important in cotton production is resistance to lepidopteran insect damage. This trait has been introduced into cotton plants and is a successful product now used in cotton production. The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421-477, 1988). For this reason, it is often necessary to screen a large number of events in order to identify an event characterized by optimal expression of a introduced gene of interest. For example, it has been observed in plants and in other organisms that there may be a wide variation in levels of expression of one or more exogenously introduced genes among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that exhibits the desired transgene expression levels and patterns for commercial purposes. An event that exhibits such desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well known nucleic acid detection method such as nucleic acid amplification techniques or nucleic acid hybridization using nucleic acid probes. These detection methods generally focus on frequently used genetic elements, such as promoters, terminators, marker genes, etc. As a result, such methods may not be useful for discriminating between different events, particularly those produced using the same, similar, or substantially related nucleic acid constructs unless the sequence of chromosomal DNA adjacent to the inserted DNA ("flanking DNA") is known. An event-specific thermal amplification assay is discussed, for example, by Windels et al. (Med. Fac. Landbouww, Univ. Gent 64/5b: 459-462, 1999), who identified glyphosate tolerant soybean event 40-3-2 using a primer set spanning the junction between the inserted heterologous DNA and flanking chromosomal DNA, specifically one primer that included sequence from the insert and a second primer that included sequence from flanking DNA, to produce an amplicon which proved to be diagnostic for the event.

SUMMARY OF THE INVENTION

According to an aspect of the invention, compositions and methods are provided for detecting the presence of various transgene/genomic insertion regions from a cotton plant designated PV-GHBK04, also known herein as cotton event 531. DNA sequences are provided that comprise at least one junction sequence of 531 identified as SEQ ID NO:1, SEQ ID NO:2, SEQ ID NO:3, SEQ ID NO:4, SEQ ID NO:32, and complements thereof; wherein a junction sequence spans the junction between heterologous DNA inserted into the genome and the DNA from the cotton cell flanking the insertion site and is diagnostic for the event.

This invention relates to the seeds and to the progeny of cotton event 531, and to methods for detecting nucleic acids contained within and produced by the event 531 in a biological or commercial sample.

According to another aspect of the invention, methods of producing a lepidopteran resistant cotton plant are provided that comprise the steps of: (a) sexually crossing a first parental cotton line comprising cotton event 531 DNA that exhibits a trait which confers resistance to one or more lepidopteran insect species upon the event, with a second parental cotton line that does not exhibit lepidopteran insect resistance, thereby producing a plurality of progeny plants; and (b) selecting a progeny plant that exhibits resistance to one or more lepidopteran insect species. The methods are useful for introgressing the lepidopteran resistance trait into different genetic backgrounds. Such methods may optionally comprise a further step of back-crossing the progeny plant to the second parental cotton line to produce a cotton plant that is also lepidopteran resistant.

According to another aspect of the invention, the DNA sequences that comprise at least 11 or more contiguous nucleotides of the DNA sequence of SEQ ID NO: SEQ ID NO:1, SEQ ID NO:2, SEQ ID NO:3, SEQ ID NO:4, SEQ ID NO:32, SEQ ID NO:12, SEQ ID NO:13, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28 and complements thereof for use as DNA primers in DNA amplification methods. The amplicons produced using these primers are diagnostic for cotton event 531.

The amplicons produced by said DNA primers are an aspect of the invention.

According to another aspect of the invention, methods of detecting the presence of DNA corresponding to the cotton event 531 event in a sample are provided. Such methods comprise: (a) contacting the sample comprising DNA with a primer set that, when used in a nucleic acid amplification reaction with DNA from cotton event 531, produces an amplicon that is diagnostic for cotton event 531 nucleic acids in a sample; (b) performing a nucleic acid amplification reaction, thereby producing the amplicon; and (c) detecting the amplicon.

According to another aspect of the invention, methods of detecting the presence of a DNA corresponding to the 531 event in a sample, such methods comprising: (a) contacting the sample comprising DNA with a probe that hybridizes under stringent hybridization conditions with DNA from cotton event 531 (i.e., does not hybridize to nucleic acid sequences which are other than DNA from cotton event 531) and does not hybridize under the stringent hybridization conditions with a control cotton plant (non-531 DNA); (b) subjecting the sample and probe to stringent hybridization conditions; and (c) detecting hybridization of the probe to the DNA.

According to another aspect of the invention, nucleic acid detection kits are provided for use in identifying the presence of cotton plant event 531 nucleic acids in a sample comprising: (a) a probe which is or is complementary to a part of the heterologous DNA sequence present in the genome of cotton plant event 531, said probe comprising at least 11 or more consecutive nucleotides, said consecutive nucleotides being selected from the group consisting of SEQ ID NO:1, SEQ ID NO:2, SEQ ID NO:3, SEQ ID NO:4, and SEQ ID NO:32, and complements thereof; (b) reagents necessary for detecting the binding of said probe to the heterologous DNA sequence inserted into the genome of cotton plant event 531; and (c) instructions for use, packaged together in said kit.

The foregoing and other aspects of the invention will become more apparent from the following detailed description and accompanying drawings.

DESCRIPTION OF THE DRAWINGS

FIG. 1 is a schematic representation of the inserted heterologous DNA in cotton event 531 representing the arrangement of the DNA inserted at a single genome locus and containing (i) A, at the indicated 3' end a cassette comprising a full length functional inserted DNA sequence from plasmid PV-GHBK04 including an nptII coding sequence and a cry1A coding sequence, and at the indicated 5' end a partial cry1A coding sequence and 7S 3' termination sequence inverted with reference to the sequence within the full length functional inserted DNA sequence; and (ii) B, a partial 7S 3' sequence which is not physically linked to the cotton event 531; wherein vertical serrated lines indicate junctions between heterologous inserted DNA and plant genomic DNA, arrows within the genetic elements imply the direction of transcription orientation, and triangles represent the border region of T-DNA sequences.

FIG. 2 illustrates the results of thermal amplification analysis of the 5' and 3' insert to plant junctions of the full length functional inserted DNA in cotton event 531, performed on genomic DNA isolated from cotton event 531 seed tissue by pairing an insert and a flanking sequence primer specific to the 5'-end of the insert (Panel A, Primers C and D, respectively) or the 3'-end of the insert (Panel B, Primers A and B, respectively); Lanes 2, 3 and 4 contain the product generated from cotton event 531 genomic DNA template, control reactions containing no template DNA (Lane 6), and Coker 312 non-transgenic control DNA (Lane 5); the location of the primers used in the analyses appear as small arrows below the illustration of the inserted DNA below the panels; triangles represent the T-DNA sequence.

DESCRIPTION OF THE SEQUENCES

Figures 3A, 3B, 3C:
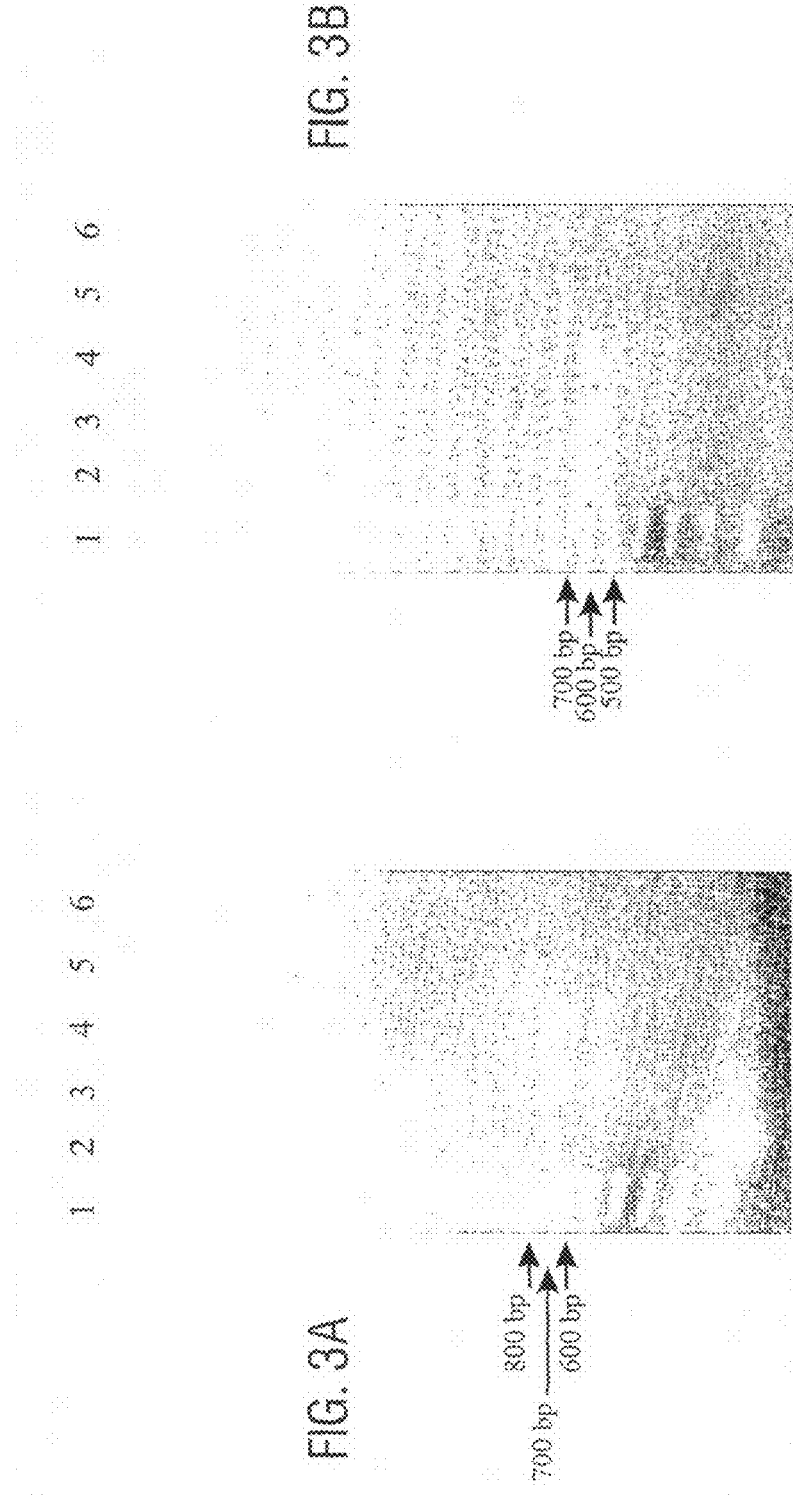
FIG. 3 illustrates the results of thermal amplification analysis of a portion of the 7S 3' sequence in cotton event 531, performed on genomic DNA isolated from cotton event 531 seed tissue by pairing an insert and a flanking sequence primer specific to the 5'-end of the insert (Panel A, Primers E and F, respectively) or the 3'-end of the insert (Panel B, Primers G and H, respectively); primers are denoted as small arrows below the diagram of the inserted DNA below the panels; Lanes 2, 3 and 4 contain the product generated from genomic DNA template of cotton event 531; control reactions containing no template (Lane 6), and Coker 312 non-transgenic control DNA (Lane 5); triangle represents T-DNA sequence.

SEQ ID NO:1 corresponds to a junction sequence which is diagnostic for the arbitrarily assigned 3' end of the full length primary functional inserted DNA sequence in cotton event 531.

SEQ ID NO:2 corresponds to a junction sequence which is diagnostic for the arbitrarily assigned 5' end of the partial cry1Ac DNA coding sequence inserted in cotton event 531.

SEQ ID NO:3 corresponds to a junction sequence which is diagnostic for the arbitrarily assigned 5' end of the full length primary functional inserted DNA sequence in cotton event 531.

SEQ ID NO:4 corresponds to a junction sequence which is diagnostic for the arbitrarily assigned 3' end of the partial 7S 3' plant transcription termination and polyadenylation sequence inserted into the genome in cotton event 531.

SEQ ID NO:5 corresponds to the sequence of the arbitrarily assigned 5' end of the partial cry1Ac DNA coding sequence inserted in cotton event 531.

SEQ ID NO:6 corresponds to the cotton genome DNA sequence which is adjacent to and flanking the 5' end of the arbitrarily assigned 5' end of the partial cry1Ac DNA coding sequence inserted in cotton event 531.

SEQ ID NO:7 corresponds to cotton genome DNA sequence which is adjacent to and flanking the 5' end of the full length primary functional inserted DNA sequence in cotton event 531.

SEQ ID NO:8 corresponds to the DNA sequence of the arbitrarily assigned 5' end of the full length primary functional inserted DNA in cotton event 531.

SEQ ID NO:9 corresponds to the cotton genome sequence adjacent to and flanking the arbitrarily assigned 3' end of the partial 7S 3' plant transcription termination and polyadenylation sequence inserted into the genome in cotton event 531.

SEQ ID NO:10 corresponds to DNA sequence of the arbitrarily assigned 3' end of the full length primary functional inserted DNA in cotton event 531.

SEQ ID NO:11 corresponds to the cotton genome DNA sequence adjacent to and flanking the arbitrarily assigned 3' end of the full length primary functional inserted DNA in cotton event 531.

SEQ ID NO:12 corresponds to a primer sequence complementary to a part of the cotton genomic DNA sequence identified as flanking the arbitrarily assigned 3' end of the full length primary functional inserted DNA sequence in cotton event 531, and produces amplicon diagnostic for cotton event 531 DNA in a sample when paired with a primer corresponding to the sequence set forth in SEQ ID NO:13 and cotton event 531 template DNA.

SEQ ID NO:13 corresponds to a primer sequence complementary to a part of the arbitrarily assigned 3' end sequence of the full length primary functional DNA inserted into the cotton genome in cotton event 531, and produces an amplicon diagnostic for cotton event 531 DNA in a sample when paired with a primer corresponding to the sequence set forth in SEQ ID NO:12 and cotton event 531 template DNA.

SEQ ID NO:14 corresponds to a sequence diagnostic for cotton event 531 DNA in a biological sample.

SEQ ID NO:15 corresponds to a sequence diagnostic for cotton event 531 DNA in a biological sample.

SEQ ID NO:16 corresponds to a sequence diagnostic for cotton event 531 DNA in a biological sample.

SEQ ID NO:17 corresponds to Primer A, a sequence which is or is complementary to a sequence within the arbitrarily assigned 3' end of the full length functional inserted DNA in event 531.

SEQ ID NO:18 corresponds to Primer B, a sequence which is or is complementary to a sequence within the 3' end flanking cotton genome sequence near the arbitrarily assigned 3' end of the full length functional inserted DNA in event 531.

SEQ ID NO:19 corresponds to Primer C, a sequence which is or is complementary to a sequence within the sequence in event 531 which is arbitrarily assigned as the 5' end of the inserted sequence linked to the full length functional inserted DNA.

SEQ ID NO:20 corresponds to Primer D, a sequence which is or is complementary to a sequence within a part of the 5' end flanking cotton genome sequence near the arbitrarily assigned 5' end of the partial cry1A coding sequence, which is linked 5' to the full length functional inserted DNA in event 531.

SEQ ID NO:21 corresponds to Primer E, a sequence which is or is complementary to the arbitrarily assigned 3' end of the partial 7S 3' sequence inserted into the cotton genome in event 531.

SEQ ID NO:22 corresponds to Primer F, a sequence which is or is complementary to a part of the 5' end flanking cotton genome sequence near the arbitrarily assigned 5' end of the partial 7S 3' sequence inserted into the cotton genome in event 531.

SEQ ID NO:23 corresponds to Primer G, a sequence which is or is complementary to the arbitrarily assigned 5' end of the partial 7S 3' sequence inserted into the cotton genome in event 531.

SEQ ID NO:24 corresponds to Primer H, a sequence which is or is complementary to a part of the 3' end flanking cotton genome sequence near the arbitrarily assigned 3' end of the partial 7S 3' sequence inserted into the cotton genome in event 531.

SEQ ID NO:25 corresponds to Primer I, a sequence which is or is complementary to a part of the 5' end flanking cotton genome sequence near the arbitrarily assigned 5' end of the partial cry1A coding sequence inserted into the genome of cotton event 531.

SEQ ID NO:26 corresponds to Primer J, a sequence which is or is complementary to a part of the 3' end flanking cotton genome sequence near the arbitrarily assigned 3' end of the full length functional inserted DNA in cotton event 531.

SEQ ID NO:27 corresponds to Primer K, a sequence which is or is complementary to a sequence within the 5' flanking cotton genome sequence near the arbitrarily assigned 5' end of the partial 7S 3' sequence present in event 531.

SEQ ID NO:28 corresponds to Primer L, a sequence which is or is complementary to a sequence within the 3' flanking cotton genome sequence near the arbitrarily assigned 3' end of the partial 7S 3' sequence present in event 531.

SEQ ID NO:29 corresponds to an amplicon sequence produced using primers corresponding to SEQ ID NO:27 and SEQ ID NO:28 together with native cotton template DNA.

SEQ ID NO:30 corresponds to an amplicon sequence produced using primers corresponding to SEQ ID NO:25 and SEQ ID NO:26 together with native cotton template DNA.

SEQ ID NO:31 corresponds to the nucleotide sequence of a part of the cotton genome flanking the arbitrarily assigned 5' end of the partial 7S 3' DNA sequence inserted into the cotton genome in event 531.

SEQ ID NO:32 corresponds to a sequence which is diagnostic for the presence of event 531 DNA in a biological sample, nucleotides 1-10 corresponding to the first 10 cotton genome nucleotides adjacent to and flanking the arbitrarily assigned 5' end of the partial 7S 3' sequence inserted into the genome in event 531, nucleotides 11-20 corresponding to the first ten nucleotides within the arbitrarily assigned 5' end of the partial 7S 3' sequence inserted into the genome in event 531.

SEQ ID NO:33 corresponds to the partial 7S 3' sequence inserted present in event 531, along with a part of the 5' and 3' cotton genome flanking sequences.

DETAILED DESCRIPTION OF THE PREFERRED EMBODIMENTS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, Genes V, Oxford University Press: New York, 1994. The nomenclature for DNA bases as set forth at 37 CFR §1.822 is used.

As used herein, the term "biological sample", or "sample", is intended to include nucleic acids, polynucleotides, DNA, RNA, tRNA, cDNA, and the like in a composition or fixed to a substrate which enables the sample to be subjected to molecular probe analysis or thermal amplification using oligonucleotide probes and/or primers.

As used herein, the term "cotton" means *Gossypium hirsutum* and includes all plant varieties that can be bred with cotton, including wild cotton species.

As used herein, the term "comprising" means "including but not limited to".

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated backcrossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987). Backcross breeding has been used to transfer genes for a simply inherited, highly heritable trait into a desirable homozygous cultivar, inbred line, or elite germplasm which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from cotton event 531 whether from a cotton plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally about 11 nucleotides or more in length, preferably 18 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods. Primers and probes are often interchangeable, and so primers may be used as probes and probes may be used as primers where effective. One skilled in the art would know how and when to use a probe as a primer and how and when to use a primer as a probe.

Methods for preparing and using probes and primers are described, for example, in *Molecular Cloning: A Laboratory Manual*, 2nd ed., vol. 1-3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. Thermal amplification primers can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and inserted heterologous sequences disclosed herein can be used to confirm (and, if necessary, to correct) the disclosed sequences by conventional methods, e.g., by re-cloning and sequencing such flanking DNA and inserted sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C.

to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO:1, SEQ ID NO:2, SEQ ID NO:3, SEQ ID NO:4, and SEQ ID NO:32 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1, SEQ ID NO:2, SEQ ID NO:3, SEQ ID NO:4, and SEQ ID NO:32 or complements or fragments of either under high stringency conditions. In one aspect of the present invention, a preferred marker nucleic acid molecule of the present invention has the nucleic acid sequence set forth SEQ ID NO:1, SEQ ID NO:2, SEQ ID NO:3, SEQ ID NO:4, SEQ ID NO:32, SEQ ID NO:14, SEQ ID NO:15, SEQ ID NO:16, and SEQ ID NO:21 or complements thereof or fragments of either. In another aspect of the present invention, a preferred diagnostic marker nucleic acid molecule of the present invention shares between from about 80% to about 100% or from about 90% to about 100% sequence identity with the nucleic acid sequence set forth in SEQ ID NO:1, 2, 3, SEQ ID NO:4, SEQ ID NO:32, SEQ ID NO:14, SEQ ID NO:15, SEQ ID NO:16, and SEQ ID NO:21 or complement thereof or fragments of either. In a further aspect of the present invention, a preferred marker nucleic acid molecule of the present invention shares between from about 95% to about 100% sequence identity with the sequence set forth in SEQ ID NO:1, SEQ ID NO:2, SEQ ID NO:3, SEQ ID NO:4, SEQ ID NO:32, SEQ ID NO:14, SEQ ID NO:15, SEQ ID NO:16, and SEQ ID NO:21 or complements thereof or fragments of either. SEQ ID NO:1, SEQ ID NO:2, SEQ ID NO:3, SEQ ID NO:4, SEQ ID NO:32, SEQ ID NO:14, SEQ ID NO:15, SEQ ID NO:16, and SEQ ID NO:21 and complements thereof may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY; all of which is herein incorporated by reference in its' entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by a thermal amplification means) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, an "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

As used herein, "transformation" refers to the transfer of a nucleic acid fragment into the genome of a host organism such as a host plant, resulting in genetically stable inheritance. Host plants containing the transformed nucleic acid fragments are referred to as "transgenic plants".

As used herein, the term "diagnostic" refers to the fact that, for the purposes of identifying nucleic acid sequences as those contained within or derived from cotton event 531, any one or more of the novel DNA sequences set forth herein comprise the cotton genome flanking sequences adjacent to and linked to the arbitrarily assigned ends of the inserted heterologous DNA sequences are necessary and sufficient as being descriptive as a distinguishing characteristic of the event 531 genome, so long as the sequence comprises at least a part of one of the ends of the inserted heterologous DNA sequence or the cotton genome sequence flanking or adjacent to one of these ends and includes at least the two nucleotides, the di-nucleotide, comprising the point at which the cotton genome sequence and the inserted heterologous DNA sequence are linked together by a phosphodiester bond. It is well known in the art that a sequence which is diagnostic for a particular event, such as those disclosed herein for event 531, which is not present in a particular sample containing nucleic acids, is indicative that the sample does not contain the diagnostic sequence and therefore the nucleic acids in the sample are not or were not derived from and have not been contained within the genome of cotton event 531. In addition, additional novel and diagnostic sequences are present within cotton event 531 DNA as exemplified herein selected from the group consisting of SEQ ID NO:1, SEQ ID NO:2, SEQ ID NO:3, SEQ ID NO:4, SEQ ID NO:32, SEQ ID NO:14, SEQ ID NO:15, SEQ ID NO:16, and SEQ ID NO:21 and complements thereof.

As used herein, "amplified DNA" or "amplicon" refers to the product of nucleic-acid amplification of a target nucleic acid sequence that is part of a nucleic acid template. For example, to determine whether the cotton plant resulting from a sexual cross contains transgenic event genomic DNA from the cotton plant of the present invention, DNA extracted from a cotton plant tissue sample may be subjected to nucleic acid amplification method using a primer pair that includes a first primer derived from sequences in the genome of the plant which are adjacent to one end of the inserted heterologous DNA sequence, and a second primer derived from sequences within the inserted heterologous DNA sequence, to produce an amplicon that is diagnostic for the presence of the event DNA. The amplicon is of a length and has a sequence that is also diagnostic for the event. The amplicon contains at least the dinucleotide sequence comprising the two nucleotides forming the link between one end of the inserted heterologous DNA and the first nucleotide within the native genome DNA sequence which is immediately adjacent to the end of the inserted heterologous DNA sequence as well as the combined sequences of the first and the second primers. The amplicon may range in length from about five hundred nucleotide base pairs, to about three hundred nucleotide base pairs, to about two hundred nucleotide base pairs, to about fifty nucleotide base pairs, to about the combined length of the primer pairs plus one nucleotide base pair. Alternatively, a primer pair can be derived from flanking sequence within the cotton plant genome sequences linked to both ends of the inserted heterologous DNA sequence so as to produce an amplicon that includes the entire insert nucleotide sequence. A member of a primer pair which is derived from the plant genomic sequence may be located a distance from either end of the inserted DNA sequence, and this distance can range from one nucleotide base pair up to about twenty thousand nucleotide base pairs. In addition, and particular to cotton event 531, are sequences which are diagnostic for the event selected from the group consisting of SEQ ID NO:1, SEQ ID NO:2, SEQ ID NO:3, SEQ ID NO:4, SEQ ID NO:32, SEQ ID NO:14, SEQ ID NO:15, SEQ ID NO:16, and SEQ ID NO:21. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. Thermal amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from cotton event 531 can be verified (and corrected if necessary) by amplifying such sequences from the event using primers derived from the sequences provided herein followed by standard DNA sequencing of the amplification products.

The amplicon produced by these methods may be detected by a plurality of techniques. One such method is Genetic Bit Analysis (Nikiforov, et al. Nucleic Acid Res. 22:4167-4175, 1994) in which an oligonucleotide is designed which overlaps both the adjacent flanking genomic DNA sequence and the inserted DNA sequence. The oligonucleotide is immobilized in wells of a microwell plate. Following thermal amplification of the region of interest (using a first primer complementary to a part of the inserted sequence and second primer complimentary to a part of the adjacent flanking genomic sequence), a single-stranded amplicon can be used to hybridize to the immobilized oligonucleotide and serve as a template for a single base extension reaction using a DNA polymerase and labelled ddNTPs specific for the expected next base, as determined by fluorescent or immunological based detection methods. A positive signal indicates the presence of the insert/flanking sequence in the sample and is diagnostic for the presence of the event 531 nucleic acid.

Another method for detecting the amplicon diagnostic for the event 531 nucleic acid in a sample is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to a single-stranded amplicon from the region of interest (amplicon produced using a first primer complimentary to a sequence within the inserted heterologous DNA sequence and a second primer complimentary to a sequence within the flanking genomic sequence) and incubated in the presence of a DNA polymerase, ATP, sulfurylase, luciferase, apyrase, adenosine 5' phosphosulfate and luciferin. dNTPs are added individually and incorporation results in the production of photons of light which are detected and measured, and which is diagnostic for the event 531 nucleic acid sequence in a sample.

Fluorescence Polarization as described by Chen, et al., (Genome Res. 9:492-498, 1999) is a method useful for detecting the diagnostic amplicon of the present invention. Using this method, an oligonucleotide is designed which overlaps the junction of the genomic flanking sequence and inserted DNA sequence. The oligonucleotide is hybridized to a single-stranded thermal amplification product from the region of interest (using a first primer complementary to a part of the inserted heterologous DNA sequence and a second primer complimentary to a part of the genomic DNA sequence flanking the proximal terminal end of the inserted heterologous DNA sequence) and incubated in the presence of a DNA polymerase and a ddNTP labeled with a fluorophore which emits a particular wavelength of light (emission spectrum) upon excitation with light of a wavelength different from the emission spectrum (excitation spectrum). Single base extension results in incorporation of the fluorphore labeled ddNTP. Incorporation can be measured as a change in fluorescence polarization using a fluorimeter. A change in fluorescence polarization indicates the presence of the transgene insert/flanking sequence within the amplicon due to successful amplification, hybridization, and single base extension, and is diagnostic for the event 531 nucleic acid in a sample.

Taqman® (PE Applied Biosystems, Foster City, Calif.) is described as a method of detecting and quantifying the presence of a DNA sequence and sufficiently described in the instructions provided by the manufacturer. Briefly, a FRET (fluorescence resonance emissions tagged) oligonucleotide probe is designed which overlaps the junction at which the reference cotton genomic DNA sequence flanking one end of the inserted heterologous DNA sequence and the end of the inserted heterologous DNA most proximal to the reference cotton genomic DNA sequence are linked. The FRET probe and thermal amplification primers (a first primer complementary to a part of the inserted heterologous DNA sequence and a second primer complementary to a part of the adjacent or flanking cotton genomic DNA sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization, and is diagnostic for the presence of the event 531 nucleotide sequence in a sample.

Molecular Beacons have been described for use in sequence detection as described in, Tyangi, et al. (Nature Biotech. 14:303-308, 1996) Briefly, a FRET oligonucleotide probe is designed that overlaps the flanking genomic and insert DNA junction. The unique structure of the FRET probe results in a probe exhibiting a secondary structure that maintains the fluorescent and quenching moieties in close proximity. The FRET probe and thermal amplification primers (one primer in the insert DNA sequence and one in the flanking genomic sequence) are cycled in the presence of a thermostable polymerase and dNTPs. Following successful thermal amplification of the amplicon diagnostic for the event 531 DNA sequence, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization, and is diagnostic for the event 531 nucleic acid in a sample.

Ligase chain reaction is also contemplated as being diagnostic for the event 531 nucleic acids in a sample.

All of the above methods can be modified to determine the zygosity of a particular sample of nucleic acids derived from a single source. For example, a cotton event 531 plant which is homozygous for the event 531 allele contains within its genome two copies of the event 531 allele characteristic of and diagnostic for the cotton event 531 genome, and thus when selfed would breed true. Alternatively, a cotton event 531 homozygous plant can be crossed with another variety of cotton, and the result of that cross would be plants that were heterozygous for the event 531 allele. Methods are envisioned in which one skilled in the art could determine the zygosity of a particular plant with reference to the event 531 allele. This method requires at least three oligonucleotide sequences as set forth herein. For example, a heterozygosity assay comprising a thermal amplification reaction comprising event 531 nucleic acid sequences in a sample as the template and Primer K (SEQ ID NO: 27) and Primer L (SEQ ID NO: 28) described herein would produce an amplicon of about 443 base pairs in length, which is diagnostic for the presence of event 531 DNA in a sample. However, the same primers would also produce an amplicon of about 209 base pairs in length, which is diagnostic for the presence of cotton DNA other than event 531 in a sample. Therefore, in a biological sample comprising cotton genomic DNA, the production of only the larger of the two sequences would indicate that the cotton plant source genome would contain only event 531 DNA. Similarly, observation of only the smaller amplicon would indicate the presence of only cotton DNA other than event 531 in the sample. However, a heterozygote plant comprising one allele corresponding to event 531, and a separate allele corresponding to native cotton genomic DNA would produce both amplicons. Many other variations on this theme are obvious to the skilled artisan now that the novel diagnostic sequences are disclosed herein.

Herein, the inventors have determined as judged by molecular characterization that cotton event 531 contains a primary functional insert containing a significant portion of the transformation plasmid, PV-GHBK04. A second nonfunctional insertion, includes a right border initiation event that continues up to and is linked with the 7S 3' transcriptional termination sequence and 3' of the Cry1A coding sequence within the primary functional insertion. A third insertion which is unlinked to the first two, i.e. does not segregate true with the first and second inserted DNA segments, consists of a part of the 7S 3' plant transcriptional termination and polyadenylation sequence. These three segments are detectable and diagnostic for the event 531 nucleic acid sequences in a sample, in particular in plants which have been selfed since the origination of the 531 event. However, upon introgression of the 531 insecticidal activity into other germplasms by crossing with other than the Coker 312 parental variety, the third segment fails to breed true and so may not produce amplicons which, as taught herein, are diagnostic for the 531 event. It should be noted that the absence of particular amplicons associated with this particular segment should not be diagnostic of a cotton plant other than the cotton plant event 531 in a sample.

The inventors herein describe the molecular analyses that have been performed on transgenic cotton event 531 to further define the ends of the T-DNA insertions and identify the cotton genomic DNA flanking the T-DNA insertions. Genome walking studies combined with nucleotide sequencing has resulted in the identification of the DNA sequences at the arbitrarily assigned 5' and 3' ends of the primary functional insert, as well as cotton genomic DNA flanking the 5' and 3' ends of the T-DNA insertions in the transgenic cotton event 531. The second, nonfunctional, T-DNA insertion, containing a portion of the cry1A coding region, is located at the arbitrarily assigned 5'end (7S 3' portion) of the primary insert.

The inventors therefore disclose herein the analysis of the genome architecture of the inserted sequence and flanking cotton genomic DNA sequences in transgenic cotton event 531 including about 309 nucleotides of cotton genomic DNA flanking the arbitrarily assigned 5'end of the insertion and about 211 base pairs of cotton genomic DNA flanking the arbitrarily assigned 3'end of the insertion event in cotton event 531. In addition, a second inserted sequence containing a part of the 3' coding region for a Cry1A nucleic acid sequence is present in proximity to the arbitrarily assigned 5'-end (7S 3' portion) of the primary insert, thus defining a complex arrangement of these genetic elements derived from the transformation plasmid PV-GHBK04 at a single point of insertion in the genome of the transgenic cotton event 531, notwithstanding the third sequence comprising the portion of a 7S 3' end sequence at an unlinked single point of insertion in the cotton genome. The second inserted sequence is effectively an inverted repeat of the terminal coding sequence for the Cry1Ac protein and associated 7S 3' termination sequence within the full length primary functional inserted DNA sequence in event 531. The physical organization of the inserted sequences is set forth in FIG. 1 herein.

A method for producing a cotton plant that is resistant to lepidopteran insect infestation may be conducted with the following steps: 1) sexually crossing a first cotton plant grown from the cotton seed event 531 comprising a DNA molecule selected from the group consisting of SEQ ID NO:14, SEQ ID NO:15, SEQ ID NO:16, and SEQ ID NO:21 that confers resistance to lepidopteran insect infestation, and a second cotton plant that lacks the resistance to lepidopteran insect infestation, thereby producing a plurality of first progeny plants;

2) selecting a first progeny plant that is resistant to lepidopteran insect infestation; 3) selfing said first progeny plant, thereby producing a plurality of second progeny plants; and 4) selecting from said second progeny plants a plant resistant to lepidopteran insect infestation. The first progeny plant that is resistant to lepidopteran insect infestation or the second progeny plant that is resistant to lepidopteran insect infestation may be backcrossed to the second cotton plant or a third cotton plant and a cotton plant that is resistant to lepidopteran insect damage infestation be produced.

DNA detection kits can be developed using the compositions disclosed herein and the methods well known in the art of DNA detection. The kits are useful for identification of cotton event 531 DNA in a sample and can be applied to methods for breeding cotton plants containing 531 DNA. The kits contain one or more DNA sequences comprising at least 11 contiguous nucleotides homologous or complementary to sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33 and complements thereof, these DNA sequences can be used in DNA amplification reactions or as probes in a DNA hybridization method.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones (see, for example, Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: Analyzing DNA, 1, Cold Spring Harbor, N.Y., 1997).

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Cotton, *Gossypium hirsutum*, has been genetically modified to resist lepidopteran pests, which have a negative impact on cotton production. This was accomplished by the insertion of a DNA cassette which encodes the insecticidal Cry1Ac protein from *Bacillus thuringiensis* into the genome of cotton cultivar Coker 312. This transformation resulted in three separate insertions into the cotton genome. The primary, full length functional inserted DNA sequence responsible for expressing the Cry1Ac protein in cotton event 531 comprises among other linked elements, a promotor, cry1Ac coding region, and termination sequence. A second insert comprises a partial cry1Ac coding region and termination sequence. The third insert comprises only a partial termination sequence. Cotton genome flanks the 5' and 3' ends of all three inserts. Therefore, six unique cotton genome/insert junctions were created as a result of the transformation process. These inserted DNA sequences are illustrated in FIG. 1 herein.

Molecular analyses were performed on cotton event 531 to define the ends of the transgene DNA insertions and identify the cotton genomic DNA flanking the transgene DNA inserts. Genome walking studies combined with nucleotide sequencing provided the DNA sequences of five of the said cotton genome/insert junctions.

The complex arrangement of genetic elements, derived from the transformation plasmid PV-GHBK04 in cotton event 531 provides novel nucleic acid sequences at the 5' and 3' cotton genome/insert junctions at each of three sites of insertions. These novel nucleic acid sequences are useful for detecting DNA from cotton event 531 in a sample using various methods well known in the art. The following provides non-limiting examples of how a skilled artisan might use these novel nucleic acid sequences to detect cotton event 531 in a sample.

Example 1

Cotton Genomic DNA Isolation

DNA from cotton event 531 was extracted from seed tissue. DNA was extracted from both seed and leaf tissues from the control substance (non-transgenic cotton seed and leaf tissue). DNA from seed was isolated by processing the seed to a fine powder using a commercially available blender. Approximately 2 grams of the processed seed was transferred to a 50 ml conical tube, and ~16 ml of CTAB extraction buffer [1.5% (w:w) CTAB, 75 mM Tris-HCl pH 8.0, 100 mM EDTA pH 8.0, 1.05 M NaCl, and 0.75% (w:w) PVP (MW 40,000)] was added to the processed seed. The samples were incubated at 65° C. for approximately 30 minutes with intermittent mixing and then allowed to cool to room temperature. An equal volume (~16 ml) of room temperature chloroform:isoamyl alcohol (24:1 (v/v)) or chloroform was added to the samples. The suspension was mixed by inversion, and the two phases separated by centrifugation at ~16,000×g for 5 minutes. The aqueous (top) layer was removed using a transfer pipet and placed into a clean 50 ml conical tube. Approximately 1/10 volume (~1.6 ml) of 10% CTAB buffer [10% (w:w) CTAB and 0.7 M NaCl] was added to the aqueous phase, which was then mixed by inversion. The samples were centrifuged at ~16,000×g for 5 minutes to separate the phases. The aqueous (upper) phase was removed, mixed with an equal volume (~15 ml) of CTAB precipitation buffer [1% (w:w) CTAB, 50 mM Tris pH 8.0, and 10 mM EDTA pH 8.0] and allowed to stand at room temperature for approximately 1 hour. The samples were centrifuged at ~10,000×g to pellet the DNA, the supernatant was decanted, and the pellet was dissolved in approximately 2 ml of high salt TE [10 mM Tris-HCl pH 8.0, 10 mM EDTA pH 8.0, and 1 M NaCl] by incubating at 37° C. with gentle swirling for approximately 2 hours. Centrifugation was performed at ~23,000×g to pellet any remaining impurities. The supernatant was removed, placed into a clean 15 ml tube, and approximately 1/10 volume (~150 µl) of 3M NaOAc, pH 5.2, and 2 volumes (~4 ml relative to the supernatant) of chilled 100% ethanol were added to precipitate the DNA. The precipitated DNA was spooled into a microfuge tube containing approximately 1 ml of 70% ethanol. The DNA was pelleted in a microfuge at maximum speed (14,000 rpm) for 5 minutes, dried, and re-dissolved in TE, pH 8.0 in a 4° C. refrigerator overnight.

The non-transgenic cotton genomic DNA used as a control was isolated from leaf tissue that was frozen in liquid nitrogen and ground into a fine powder using a mortar and pestle. Approximately 1 g of the ground leaf tissue was transferred to a 13 ml centrifuge tube and 6 ml of extraction buffer [2.5 ml DNA extraction buffer (350 mM sorbitol, 100 mM Tris pH 7.5, 5 mM EDTA, 0.38% (w/v) sodium bisulfite), 2.5 ml nuclei lysis buffer (200 mM Tris pH 7.5, 50 mM EDTA, 2 M NaCl, 2% (w/v) CTAB), and 1 ml Sarkosyl (5% (w/v) solution)] was added. The samples were incubated at 65° C. for approximately 30 minutes with intermittent mixing. Four and a half milliliters of chloroform:isoamyl alcohol (24:1 (v/v)) at room temperature was added to the samples. The suspension was mixed for 2 to 3 minutes, and the two phases separated by centrifugation for 15 minutes at ~2,000×g at 4° C. The aqueous (top) layer was removed using a transfer pipet and placed into a 13 ml centrifuge tube. Five milliliters of 100% isopropanol were added, and the tubes were mixed by inversion to precipitate the DNA. The precipitated DNA was spooled into a microfuge tube containing 500 l of 70% ethanol. The DNA was pelleted in a microfuge at maximum speed (14,000 rpm) for 2 minutes. The DNA was dried and dissolved in TE buffer in a 4° C. refrigerator overnight.

Example 2

Identification of Unique Insert-Cotton Genome Junctions in Cotton Event 531

The DNA sequences of five cotton genome/insert junctions were identified using the PCR-based Universal GenomeWalker Kit™ as per the manufacturer's protocol followed by nucleotide sequencing of the PCR products. PCR assays were developed using one primer complementary to cotton genomic DNA and another primer complementary to inserted transgene DNA.

Identification of Diagnostic Insert-Cotton Genome Junctions within the Primary Full Length and Functional Inserted DNA Sequence For example, a first primer, Primer D (SEQ ID NO:20), designed to hybridize to the genome sequence flanking the 5' end partial cry1Ac coding sequence was paired with a second primer, Primer C (SEQ ID NO:19) designed to hybridize to the inserted sequence within the inserted partial cry1Ac coding sequence, and a third primer, Primer A (SEQ ID NO:17) designed to hybridize to a sequence within the arbitrarily assigned 3' end of the full length primary functional inserted DNA sequence was paired with a fourth primer, Primer B (SEQ ID NO:18) designed to hybridize to the genome sequence flanking the arbitrarily assigned 3' end of the full length primary functional inserted DNA sequence.

The PCR assays were performed using 10-100 ng of cotton event 531 genomic DNA template in a 50 µl reaction volume containing a final concentration of 1.1 mM $Mg^{2+}$, 0.4 µM of each primer, 200 µM each dNTP, and 2.5 units of Taq DNA polymerase. The reactions for the PCR assays were performed under the following cycling conditions: 1 cycle at 94° C. for 3 minutes; 38 cycles of 94° C. for 30 seconds, 60° C. for 30 seconds, 72° C. for 90 seconds; 1 cycle at 72° C. for 10 minutes. The PCR products were separated using agarose gel electrophoresis, visualized by ethidium bromide staining, excised from the gel, and subjected to DNA sequencing using dye-terminator chemistry to confirm the sequences.

As expected, the control reactions without template DNA and Coker 312 non-transgenic negative control DNA did not generate a PCR product. The cotton event 531 samples generated the expected size PCR products of about 1411 bp (SEQ ID NO:15) for the 5' flanking sequence and about 589 bp (SEQ ID NO:14) for the 3' flanking sequence. Therefore, the novel nucleic acid sequences at the junction of inserted DNA and cotton genomic DNA in cotton event 531 are useful for detecting DNA derived from cotton event 531 in a sample. The amplicon products were sequenced to determine the precise sequence of the flanking sequence-insert junctions. The sequence of SEQ ID NO:15 is comprised of a part of the 5' end flanking cotton genome sequence (SEQ ID NO:6) upstream or 5' to the 5' end of the partial cry1Ac coding sequence fragment, SEQ ID NO:6 being physically linked at its 3' end to the arbitrarily assigned 5' end of the inserted partial cry1Ac coding sequence (SEQ ID NO:5). The last ten nucleotides set forth in SEQ ID NO:6 and the first ten nucleotides set forth in SEQ ID NO:5 correspond to SEQ ID NO:2 which is a sequence diagnostic for the event 531 DNA in a sample. Specifically, a sequence of at least eleven nucleotides in length selected from the sequences in SEQ ID NO:15 which comprises at least the di-nucleotide in SEQ ID NO:2 from position 10 through position 11 and complements thereof are diagnostic for the cotton event 531 nucleic acid sequences in a sample. In addition the sequence of SEQ ID NO:14 is comprised of a part of the 3' end flanking cotton genome sequence (SEQ ID NO:11) downstream or 3' to the arbitrarily assigned 3' end of the primary full length and functional inserted DNA sequence in event 531, SEQ ID NO:11 being physically linked at its 5' end to the arbitrarily assigned 3' end of the primary full length and functional inserted DNA sequence in event 531 (SEQ ID NO:10). The last ten nucleotides of SEQ ID NO:10 and the first ten nucleotides of SEQ ID NO:11 comprise a 20mer nucleotide sequence set forth in SEQ ID NO:1 which is diagnostic for the event 531 DNA in a sample. Specifically, a sequence of at least eleven nucleotides in length selected from the sequences in SEQ ID NO:14 which comprises at least the di-nucleotide in SEQ ID NO:1 from position 10 through position 11, and complements thereof, are diagnostic for the cotton event 531 nucleic acid sequences in a biological sample.

Thermal amplification assays were also developed to determine the 5' end flanking sequence corresponding to the termination sequence-genome junction within the full length functional inserted sequence. The DNA sequence within the termination sequence of the 7S 3' termination sequence linked to the full length cry1Ac coding sequence inserted into Coker 312 resulting in the event 531 genome was determined, along with sequence beyond the termination sequence and out into the flanking sequence region. The resulting sequence consists of the sequence set forth in SEQ ID NO:16, and is comprised of sequences set forth in SEQ ID NO:7 (flanking cotton genome sequence 5' to, upstream of, or adjacent to the inserted DNA sequence) and SEQ ID NO:8 (7S 3' inserted DNA sequence within the primary full length and functional inserted DNA sequence). The 20mer sequence set forth in SEQ ID NO:3 comprising the junction of SEQ ID NO:7 and SEQ ID NO:8 is diagnostic for the event 531. Specifically, a sequence of at least eleven nucleotides in length selected from the sequences in SEQ ID NO:16 which comprises at least the di-nucleotide in SEQ ID NO:3 from position 10 through position 11, and complements thereof, are diagnostic for the cotton event 531 nucleic acid sequences in a biological sample.

Identification of Diagnostic Insert-Cotton Genome Junctions within the Partial 7S 3' Inserted Sequence Primers E (SEQ ID NO:21) and F (SEQ ID NO:22) were designed to amplify a sequence comprising the arbitrarily assigned 5' end of the partial 7S 3' sequence inserted into the cotton genome linked to the cotton flanking genome sequence 5' to the inserted sequence. An amplicon comprising a diagnostic sequence as set forth in SEQ ID NO:32 is obtained when these primers, as a primer pair or primer set, are used in a thermal amplification reaction along with cotton event 531 template DNA in a sample. A sequence comprising at least eleven nucleotides in length selected from the sequences as set forth in SEQ ID NO:32 and which contain at least the di-nucleotide in SEQ ID NO:32 from position 10 through position 11, and complements thereof, are diagnostic for the cotton event 531 nucleic acid sequences in a biological sample.

Primers G (SEQ ID NO:23) and H (SEQ ID NO:24) were designed to amplify a sequence comprising the arbitrarily assigned 3' end of the partial 7S 3' sequence inserted into the cotton genome linked to the cotton flanking genome sequence 3' to the inserted sequence. The 5' and 3' genomic DNA sequences flanking the second insert containing a portion of the 7S 3' genetic element were identified using one primer designed to the 5' or 3' genomic DNA sequence flanking the insertion (Primers F and H, respectively), paired with a second primer in the insertion (Primers E and G, respectively). The PCR analyses were conducted using 100 ng of genomic DNA template in a 50 µl reaction volume containing a final concentration of 1.5 mM $Mg^{2+}$, 0.2 µM of each primer, 200 µM each dNTP, and 1 unit of Taq DNA polymerase. The reactions were performed under the following cycling conditions: 1 cycle at 94° C. for 3 minutes; 38 cycles of 94° C. for 30 seconds, 60° C. for 30 seconds, 72° C. for 1.5 minutes; 1 cycle at 72° C. for 10 minutes. The PCR products were separated on 1.0% agarose gels and visualized by ethidium bromide staining. The PCR products generated from cotton event 531 DNA were excised from the gel, and subjected to DNA sequencing using dye-terminator chemistry to confirm the sequences.

An amplicon comprising a diagnostic sequence as set forth in SEQ ID NO:4 is obtained when these primers, as a primer pair or primer set, are use in a thermal amplification reaction along with cotton event 531 template DNA in a sample. A sequence comprising at least eleven nucleotides in length selected from the sequences as set forth in SEQ ID NO:4 and which contain at least the di-nucleotide in SEQ ID NO:4 from position 10 through position 11, and complements thereof, are diagnostic for the cotton event 531 nucleic acid sequences in a biological sample.

Example 3

Identification of the Native Cotton Genome Sequences into which Heterologous DNA Sequences were Inserted to Form Cotton Event 531 and Heterozygosity Assays Developed Therefrom Amplicons useful for determining the heterozygosity or homozygosity of the cotton genome with reference to event 531 are required in order to determine conclusively whether a particular line of cotton comprises event 531 sequences or otherwise.

Primers for use in detecting the native cotton genomic DNA sequence in a sample were designed which, when used with a template cotton genome DNA comprising DNA derived from other than an event 531 source, produce an amplicon which is diagnostic for at least one allele present in the template which is representative of native cotton genomic DNA uninterrupted by the inserted DNA found in event 531. For example, a primer pair consisting of Primer I (SEQ ID NO:25) which is or is complementary to cotton genome sequences within a part of the genome flanking the arbitrarily assigned 5' end of the partial cry1Ac coding sequence in event 531, and Primer J (SEQ ID NO:26) which is or is complementary to cotton genome sequences within a part of the genome flanking the arbitrarily assigned 3' end of the primary full length and functional inserted DNA in event 531, when used together in a thermal amplification reaction with cotton template DNA other than event 531 DNA produce an amplicon comprising 374 base pairs in length, one strand of which corresponds to the sequence set forth in SEQ ID NO:30, and which is diagnostic for the presence of a DNA sequence in a biological sample derived from a cotton genome other than event 531. PCR analyses of the functional insert site were performed using a primer specific to the genomic DNA sequence flanking the 5'-end of the insertion in the forward direction (Primer I), paired with a second primer specific to the genomic DNA sequence flanking the 3'-end of the insertion (Primer J). The PCR analyses were conducted using 20 ng of genomic DNA template in a 50 µl reaction volume containing a final concentration of 1.5 mM $Mg^{2+}$, 0.4 µM of each primer, 200 µM each dNTP, and 2.5 units of Taq DNA polymerase. The reactions were performed under the following cycling conditions: 94° C. for 3 minutes; 38 cycles at 94° C. for 30 seconds, 60° C. for 30 seconds, 72° C. for 1.0 minute; 1 cycle at 72° C. for 10 minutes. The PCR products were separated on a 1.5-2.0% agarose gel and visualized by ethidium bromide staining. Following electrophoresis, PCR products generated from Coker 312 non-transgenic DNA were excised from the gel and sequenced using dye-terminator chemistry.

Primers for use in detecting the native cotton genomic DNA sequence in a sample were designed which, when used with a template cotton genome DNA comprising DNA derived form other than an event 531 source, produce an amplicon which is diagnostic for at least one allele present in the template which is representative of native cotton genomic DNA uninterrupted by the inserted DNA found in event 531. For example, a primer pair consisting of Primer K (SEQ ID NO:27) which is or is complementary to cotton genome sequence within a part of the genome flanking the arbitrarily assigned 5' end of the partial 7S 3' sequence inserted in event 531, and Primer L (SEQ ID NO:28) which is or is complementary to cotton genome sequences within a part of the genome flanking the arbitrarily assigned 3' end of the partial 7S 3' sequence inserted into event 531, when used together in a thermal amplification reaction with cotton template DNA other than event 531 DNA produce an amplicon comprising 209 base pairs in length, one strand of which corresponds to the sequence set forth in SEQ ID NO:29, and which is diagnostic for the presence of a DNA sequence in a biological sample derived from a cotton genome other than event 531. An amplicon spanning the insertion site of the partial 7S 3' sequence was generated from Coker 312 non-transgenic DNA. The insertion site was amplified from Coker 312 using one primer specific to the genomic DNA sequence identified 5' of the insert DNA (Primer K) and a second primer specific to the genomic DNA sequence identified 3' of the inserted DNA (Primer L). The PCR analyses were conducted using 20 ng of genomic DNA template in a 50 µl reaction volume containing a final concentration of 1.5 mM $Mg^{2+}$, 0.4 µM of each primer, 200 µM each dNTP, and 2.5 units of Taq DNA polymerase. The reactions were performed under the following cycling conditions: 94° C. for 3 minutes; 38 cycles at 94° C. for 30 seconds, 60° C. for 30 seconds, 72° C. for 1.0 minutes; 1 cycle at 72° C. for 10 minutes. The PCR products were separated on a 2.0% agarose gel and visualized by ethidium bromide staining. Following electrophoresis, PCR products generated from Coker 312 non-transgenic DNA were excised from the gel and sequenced using dye-terminator chemistry.

Those of skill in the art, in light of these examples, should appreciate that many changes can be made to the foregoing assays to detect DNA derived from cotton event 531 in a sample. For example, a primer set comprising one primer complementary to cotton genome DNA and another primer complementary to sequences within the insert are envisioned. Furthermore, any of various hybridization assays described earlier using DNA probes complementary to said novel nucleic acid sequences located at transgene/genome junctions are envisioned as well.

The invention claimed is:

1. A DNA detection kit comprising:
   (1) at least one DNA molecule of at least 30 contiguous nucleotides homologous or complementary to SEQ ID NO:14, wherein said DNA molecule comprises SEQ ID NO:1 and wherein said DNA molecule functions as a DNA probe specific for cotton event 531; and
   (2) a list of instructions on how to identify cotton event 531.

2. A method of detecting SEQ ID NO:1 in a DNA sample comprising cotton event 531, the method comprising:
   (a) contacting said sample with a pair of primers; wherein said pair of primers is selected from the group consisting of SEQ ID NO:12 and the reverse complement of SEQ ID NO:13 and SEQ ID NO:17 and the reverse complement of SEQ ID NO:18;
   (b) performing a nucleic acid amplification reaction, thereby producing an amplicon comprising SEQ ID NO:1; and
   (c) detecting the amplicon.

3. A method of detecting SEQ ID NO:2 in a sample comprising cotton event 531, the method comprising:
   (a) contacting said sample with a pair of primers wherein said pair of primers is SEQ ID NO. 19 and the reverse complement of SEQ ID NO:20;
   (b) performing a nucleic acid amplification reaction, thereby producing an amplicon comprising SEQ ID NO:2; and
   (c) detecting the amplicon.

4. A method for detecting event 531 in a sample, said method comprising the steps of (a) contacting said sample with a probe specific for event 531, wherein said probe comprises at least 30 contiguous nucleotides homologous or complementary to SEQ ID NO:14 and comprises SEQ ID NO:1, or wherein said probe comprises at least 30 contiguous nucleotides homologous or complementary to SEQ ID NO:15 and comprises SEQ ID NO:2;
   (b) subjecting the sample and probe to stringent hybridization conditions; and
   (c) detecting hybridization of the probe to the sample.

5. A kit comprising:
   (a) a pair of polynucleotide primers for use in producing in a DNA amplification reaction an amplicon diagnostic for the presence of cotton event 531 DNA in a sample, wherein a first primer of said pair comprises at least 30 contiguous nucleotides from the cotton genome portion of SEQ ID NO:14, and a second primer of said pair comprises at least 30 contiguous nucleotides complementary to the heterologous insert DNA portion of SEQ ID NO:14, and wherein said amplicon comprises SEQ ID NO:1; and
   (b) a list of instructions on how to identify cotton event 531.

6. A DNA detection kit comprising:
   (1) at least one DNA molecule of at least 30 contiguous nucleotides homologous or complementary to SEQ ID NO:15, wherein said DNA molecule comprises SEQ ID NO:2, and wherein said DNA molecule functions as a DNA probe specific for cotton event 531; and
   (2) a list of instructions on how to identify cotton event 531.

7. An amplicon comprising 50-589 contiguous nucleotides of SEQ ID NO:14, wherein said amplicon comprises SEQ ID NO:1 or full complements thereof.

8. An amplicon comprising 50-1413 contiguous nucleotides of SEQ ID NO:15, wherein said amplicon comprises SEQ ID NO:2 or full complements thereof.

9. An isolated polynucleotide consisting of SEQ ID NO:14 or SEQ ID NO:15.

10. A method for detecting the presence of event 531 in a sample, said method comprising the steps of:
   (a) contacting said sample with a primer pair selected from the group consisting of: (i) a pair wherein a first primer of said pair comprises at least 30 contiguous nucleotides from the cotton genome portion of SEQ ID NO:14, and a second primer of said pair comprises at least 30 contiguous nucleotides complementary to the heterologous insert DNA portion of SEQ ID NO:14; and (ii) a pair wherein a first primer of said pair comprises at least 30 contiguous nucleotides from the cotton genome portion of SEQ ID NO:15; and a second primer of said pair comprises at least 30 contiguous nucleotides complementary to the heterologous insert DNA portion of SEQ ID NO:15;
   (b) producing an amplicon diagnostic for the presence of event 531 DNA in a sample, produced from the genome DNA of event 531, wherein said amplicon comprises a nucleotide sequence selected from the group consisting of SEQ ID NO:1, SEQ ID NO:2, and full complements thereof; and
   (c) detecting said amplicon.

11. A kit comprising:
   (a) pair of polynucleotide primers for use in producing in a DNA amplification reaction an amplicon diagnostic for the presence of cotton event 531DNA in a sample, wherein a first primer of said pair comprises at least 30 contiguous nucleotides from the cotton genome portion of SEQ ID NO:15, and a second primer of said pair comprises at least 30 contiguous nucleotides complementary to the heterologous insert DNA portion of SEQ ID NO:15, and wherein said amplicon comprises SEQ ID NO:2; and
   (b) a list of instructions on how to identify cotton event 531.

* * * * *